(12) United States Patent
Kepka et al.

(10) Patent No.: US 7,462,362 B2
(45) Date of Patent: Dec. 9, 2008

(54) ANTIFUNGAL NAIL COAT AND METHOD OF USE

(75) Inventors: Stanley W. Kepka, Ringoes, NJ (US); Y. Joseph Mo, Princeton, NJ (US); Hang-Yong Wang, East Brunswick, NJ (US); Mingqi Lu, Lawrenceville, NJ (US); William R. Pfister, Robbinsville, NJ (US)

(73) Assignee: NexMed Holdings, Inc., East Windsor, NJ (US)

( * ) Notice: Subject to any disclaimer, the term of this patent is extended or adjusted under 35 U.S.C. 154(b) by 756 days.

(21) Appl. No.: 10/514,190

(22) PCT Filed: Mar. 22, 2004

(86) PCT No.: PCT/US2004/008618

§ 371 (c)(1),
(2), (4) Date: Nov. 10, 2004

(87) PCT Pub. No.: WO2004/084826

PCT Pub. Date: Oct. 7, 2004

(65) Prior Publication Data

US 2006/0067898 A1    Mar. 30, 2006

Related U.S. Application Data

(60) Provisional application No. 60/456,684, filed on Mar. 21, 2003.

(51) Int. Cl.
*A61K 8/00* (2006.01)
*A61K 8/18* (2006.01)

(52) U.S. Cl. .................... 424/401; 424/61; 424/808

(58) Field of Classification Search ............... None
See application file for complete search history.

(56) References Cited

U.S. PATENT DOCUMENTS

| | | |
|---|---|---|
| 4,957,730 A | 9/1990 | Bohn et al. |
| 6,019,988 A | 2/2000 | Parab et al. |
| 6,143,793 A | 11/2000 | Laugier et al. |
| 6,495,124 B1 | 12/2002 | Samour |
| 2003/0235541 A1 | 12/2003 | Maibach et al. |

FOREIGN PATENT DOCUMENTS

| | | | |
|---|---|---|---|
| CA | 1 175 355 | | 2/1984 |
| EP | 0 515 312 A2 | | 11/1992 |
| EP | 1 138 314 A2 | | 10/2001 |
| GB | 2 202 743 A | | 10/1988 |
| WO | WO 01/60325 A1 | | 8/2001 |
| WO | WO02/02503 | * | 1/2002 |

OTHER PUBLICATIONS

M. Fujii, et al., "Enhancement of Skin Permeation of Miconazole by Phospholipid . . . ", Int'l Journal of Pharmaceutics, vol. 234, pp. 121-128 (2002).
Penlac Nail Lacquer, Physicians' Desk Reference, pp. 1219-1222 (2003).
Wester, et al., "Getting Inside The Human Nail Plate," Maibach (ed), Cosmetics & Toiletries, vol. 118, No. 5, pp. 32-38, Allured Publishing Corporation, (2003).

* cited by examiner

*Primary Examiner*—Frederick Krass
*Assistant Examiner*—Marcos Sznaidman
(74) *Attorney, Agent, or Firm*—Olson & Cepuritis, Ltd.

(57) ABSTRACT

A dual action antifungal nail coat composition and method of use for ameliorating or preventing fungal infection of the nails, and onychomycosis, in particular, is disclosed. Composition embodiments in the form of one-coat type and two-coat type suitable for daily fungicidal regimens are disclosed. A preferred antifungal nail coat composition comprises an effective fungicidal amount of antifungal agent, a permeation enhancing amount of a substantially non-volatile, permeation enhancer, a film-forming amount of a hydrophilic polymer, and a pharmaceutically acceptable, volatile carrier. The composition provides a substantially water-soluble fungicidal coating on contacting a fungally susceptible or infected nail.

1 Claim, 4 Drawing Sheets

ANTIFUNGAL NAIL COAT AND METHOD OF USE

CROSS-REFERENCE TO RELATED APPLICATION

This application claims the priority of U.S. Provisional application for Patent Ser. No. 60/456,684, filed Mar. 21, 2003, which is incorporated herein by reference.

TECHNICAL FIELD OF THE INVENTION

This invention relates to topical antifungal compositions useful for ameliorating or preventing onychomycoses of the toenails or fingernails, as well as adjacent skin. More particularly, the invention relates to a dual action antifungal nail coat composition and the method for applying the antifungal composition to a fungally susceptible or infected nail and/or adjacent skin.

BACKGROUND OF THE INVENTION

Superficial fungal infections of skin, hair, nails, or mucous membranes, are still very common among all populations. In particular, onychomycosis is a fungal infection of the nails. The onychomycosis are frequent, involving up to about 15% of persons between the ages of 40 and 60 years. Some estimates suggest that onychomycosis affects about 6 to about 13% of the North American population, with an estimated 4.9 to 12.3 million people being affected in the United States. In European populations, the estimated overall prevalence of onychomycosis is in the range of about 3 to about 10%.

Delivery of antifungal agents through the nail into the nail bed and surrounding skin has been minimally effective for the treatment of onychomycosis (infections of the fingernails, toenails, and immediate adjacent surrounding skin) in the form of a nail lacquers, primarily because the film forming water-insoluble polymers used limit the diffusion of the drug from the dried film into the nail and skin, and because previous nail lacquer compositions do not contain the optimum balance of permeation enhancement to deliver the drug to both the nail and surrounding skin in an amount sufficient for optimal antifungal activity.

Fungal infection of the nails, commonly referred to as onychomycosis, is most frequently caused by dermatophytes, but can also be caused by molds and *Candida* sp. Onychomycosis is predominantly present in toenails rather than fingernails, in males, and in the elderly. Onychomycosis is most commonly caused by *Trichophyton rubrum* (*T. rubrum*), *Trichophyton mentagrophytes* (*T. mentagrophytes*), and *Epidermophyton floccusum* (*E. floccusum*). Onychomycosis due to nondermatophytes is usually caused by *Candida* species, such as *Candida albicans*, and is more likely to cause invasive nail disease in fingernails than in toenails of immunocompetent individuals.

Onychomycosis has medical significance especially in individuals having certain diseases, such as diabetes and others where the individual is immunocompromised. Also onychomycosis can have a substantial undesirable effect on daily living activities, such as ambulation, and spontaneous remission is rare. The current treatments of onychomycosis include oral administration of antifungal agents, such as itraconazole (distributed under the tradename, SPORONOX®, by Ortho Biotech Products L.P.), and terbinafine (distributed under the tradename, LAMISIL®, by Novartis Pharmaceuticals Corporation). While itraconazole and terbinafine hydrochloride offer significant cure rates, shorter treatment regimens and lower levels of adverse events compared to the imidazoles (e.g., ketoconazole), clinically significant drug interactions can occur and the therapeutic period requires at least a few months. Thus, there is an ongoing need and desire for a non-oral management of onychomycosis.

One attempt has been made employing the antifungal agent, ciclopirox distributed commercially under the trade name PENLAC™ Nail Lacquer by Dermik Laboratories, Inc.), as an 8% topical solution containing a water-insoluble, film-forming polymer, and is described in U.S. Pat. No. 4,957,730 to Bohn, et al. Another antifungal nail lacquer compositions utilizing a water-insoluble film forming polymer is described in U.S. Pat. No. 6,495,124 by Samour. Yet another nail lacquer formulation contains 5% amorolfine, a morpholine derivative, and is manufactured by Roche Laboratories under the trade name LOCERYL™. However, water-insoluble film-forming polymers, such as used in conventional nail lacquer compositions are fast drying (less than one minute) solution of water-insoluble polymers and, if brushed onto the skin area surrounding the nail, tend to irritate the skin area. Additionally, such traditional, water-insoluble, fast drying, film-forming polymers produce high viscosity nail lacquer compositions and thus limit the mobility and time for active exchange of the antifungal agent between the film and the nail plate resulting in loss of treatment efficacy. In some instances, the nail lacquers are suitable only for treatment of mild onychomycosis without nail matrix involvement, and systemic treatment is still required for severe onychomycosis involving the nail bed.

An attempt employing azole derivatives at 0.5-1% concentration applied from a composition containing water-insoluble fatty components, solubilizers and a quick drying, water-soluble, polyvinylpyrrolidone, or vinylacetate copolymers and terpolymers thereof, is described in Canadian Patent No. 1,175,355 and European Patent No. 055,397.

The present dual action antifungal topical nail coat compositions and methods provide a fungicidal regimen suitable for the treatment of onychomycosis of varying severities in mammals in need of such treatment.

SUMMARY OF THE INVENTION

A dual action antifungal nail coat composition containing an antifungal agent for ameliorating or preventing fungal infections of nails and surrounding skin, and onychomycosis in particular, is disclosed. The present composition delivers the active ingredient both through the nail plate as well as through the surrounding skin tissue. Also disclosed are methods for topically applying the dual action antifungal nail coat composition to a fungally-susceptible or infected nail. The bioavailability of the antifungal agent is optimized by the practice of the present invention.

The antifungal nail coat compositions can be formulated as "one-coat" type and "two-coat" type compositions.

A preferred one-coat type antifungal nail coat composition embodiment comprises:

an effective fungicidal amount of an antifungal agent;

a permeation enhancing amount of a substantially non-volatile, permeation enhancer selected from the group consisting of an N,N-di($C_1$-$C_8$) alkylamino substituted, ($C_4$-$C_{18}$) alkyl ($C_2$-$C_{18}$) carboxylic ester or pharmaceutically acceptable acid addition salt thereof, a pharmaceutically acceptable alcohol, and mixtures thereof;

a film-forming amount of a hydrophilic polymer; and a pharmaceutically acceptable, volatile organic carrier.

In a one-coat type, dual action antifungal nail coat composition, the organic carrier preferably assists in distributing the drug, i.e., the antifungal agent, substantially uniformly on contact of the nail coat composition with a fungally susceptible or infected nail and or adjacent skin and volatilizes, within about one to five minutes following application to provide a substantially water-soluble, fungicidal film coating on the nail and adjacent skin tissue containing the drug and one or more substantially non-volatile penetration enhancer for on-going amelioration or prevention of fungal infection.

Another preferred dual action antifungal nail coat composition is a two-coat type composition comprising:

a first antifungal nail coat composition for providing an antifungal primer coat, comprising an effective fungicidal amount of antifungal agent dispersed in a pharmaceutically acceptable, volatile organic carrier;

a second antifungal nail coat composition for providing an antifungal film coat, comprising a film-forming amount of hydrophilic polymer, an effective fungal amount of antifungal agent, and a pharmaceutically acceptable, volatile organic carrier, and wherein either one of the first or second antifungal nail coat composition optionally includes a substantially non-volatile permeation enhancer.

In a two-coat type, dual action composition, the antifungal agent is quickly released from the first antifungal nail coat composition to a fungally-susceptible or infected nail on contact therewith to provide a fungicidal primer coat. The second antifungal nail coat composition provides a fungicidal film coat over the foregoing fungicidal primer-coated nail on subsequent contact therewith. The fungicidal film coat provides a depot for additional antifungal agent which can be released over an extended time period and provides a protective nail barrier to maintain sustained release of antifungal agent from the primer coat to the nail to optimize the topical bioavailability of antifungal agent, and to minimize further accessibility of fungal spores from the environment to the infected nail.

The antifungal agent is preferably selected from the group consisting of allylamine and azole antifungals. The allylamine antimycotic terbinafine, usually as terbinafine hydrochloride, is particularly preferred. The azole antifungals include azoles, imidazoles, as well as triazoles.

The hydrophilic polymer may be a film-forming polymer comprising a vinylpyrrolidone monomer unit, including homopolymers (such as, polyvinylpyrrolidone), copolymers, and complexes thereof, a gum, a resin, or the like. Preferably, the hydrophilic polymer is polyvinylpyrrolidone (PVP).

The volatile organic carrier preferably is a pharmaceutically acceptable aliphatic alkanol having 2 to about 5 carbon atoms, and more preferably is ethanol.

Particularly preferred substantially non-volatile permeation enhancers are dodecyl-2-(N,N-dimethylamino) isopropionate (DDAIP), benzyl alcohol and combinations thereof.

The dual action antifungal nail coat compositions of this invention can include one or more penetration enhancers in an amount effective to achieve an antifungal concentration of the antifungal drug in the nail and surrounding skin, as well as an auxiliary anti-infective, such as an antibacterial agent, an antiseptic agent, and the like, to augment the efficacy of the treatment.

Fungal infection of a toenail or fingernail may be ameliorated or prevented by fungicidal regimens in which the disclosed dual action antifungal topical nail coat compositions are applied in the form of either a one-coat type or a two-coat type by the methods described herein. The methods of this invention are preferably performed at least once a day for as long as needed to ameliorate or prevent fungal infection.

The practice of this invention using dual action antifungal nail coat compositions is desired for increasing the topical bioavailability of an antifungal drug, especially in the treatment of onychomycoses of the toenails or fingernails. Beneficially, the dual action antifungal nail coat composition can shorten the total therapeutic period, avoid or eliminate adverse systemic events usually associated with oral therapies, and improve clinical efficacy.

DETAILED DESCRIPTION OF PREFERRED EMBODIMENTS

Figure 1:
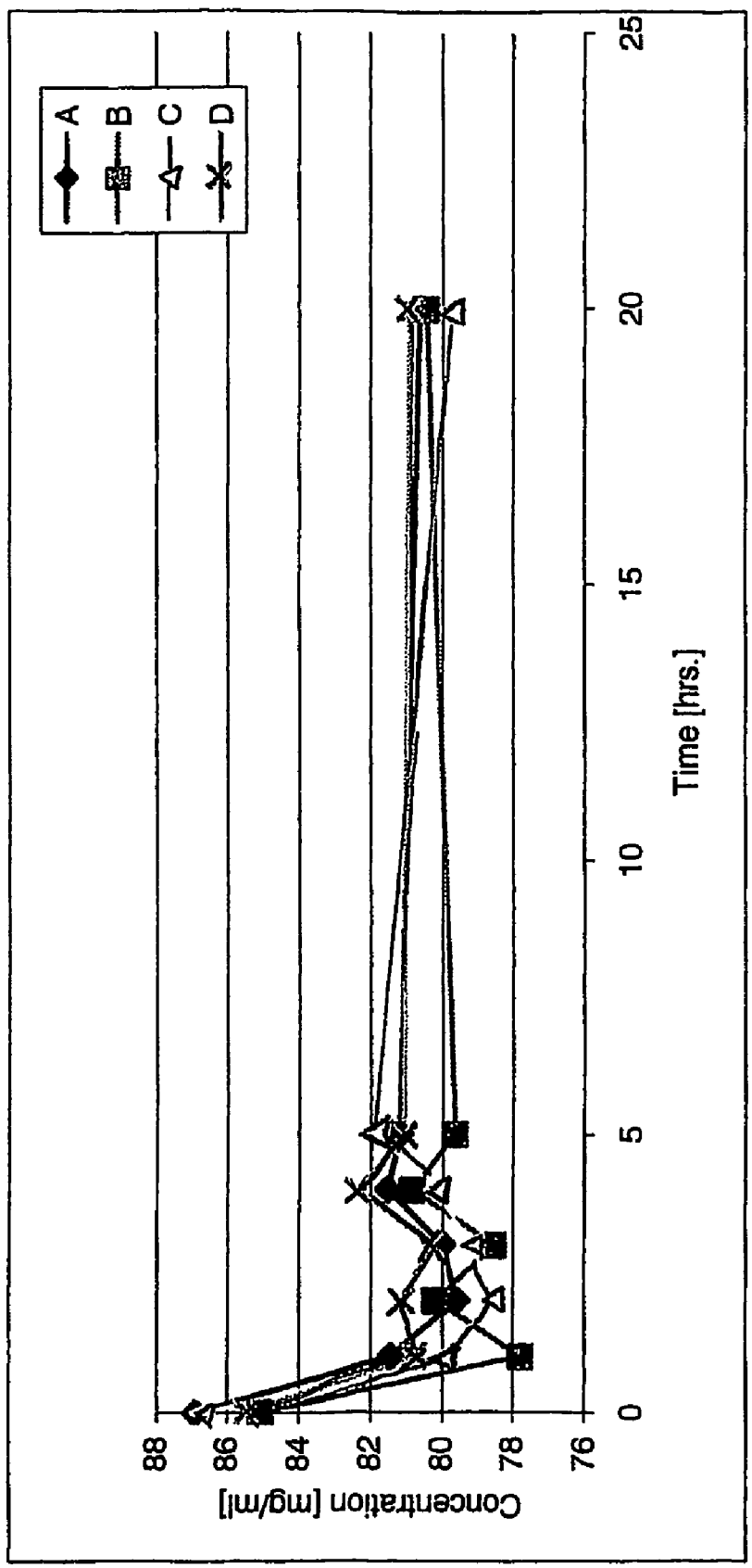
FIG. 1 is a graphical representation of terbinafine uptake by human nail clippings from a selected individual expressed as the concentration of terbinafine remaining in a terbinafine source solution as a function of time, wherein Solution A was 10 weight percent terbinafine hydrochloride in anhydrous ethanol, Solution B was 10 weight percent terbinafine hydrochloride in anhydrous ethanol plus 10 weight percent of polyvinylpyrrolidone (K-30), Solution C was 10 weight percent terbinafine hydrochloride in anhydrous ethanol plus 0.5 weight percent DDAIP.HCl, and Solution D was 10 weight percent terbinafine hydrochloride in anhydrous ethanol plus 1 weight percent DDAIP.HCl.

The term "dual action" as applied to antifungal nail coat compositions of this invention means that the nail coat composition provides a water-soluble, fungicidal film coating that contains the antifungal drug on the nail and adjacent skin tissue, and a substantially non-volatile penetration enhancer that promotes the penetration of antifungal drug into the nail as well as surrounding skin tissue.

There is no particular limitation on the antifungal agents useful for the dual action antifungal nail coat compositions of this invention, as long as the antifungal agent is effective against fungi known to cause infections of the toenails or fingernails, as well as surrounding skin, and onychomycosis, in particular. A listing of antifungal agents, without limitation thereto, may be found, for example, in the Thirteenth Edition of *The Merck Index* (2001) under the headings "Antifungal (Antibiotic)" and "Antifungal (Synthetic)" in the Therapeutic Category and Biological Activity Index section incorporated herein by reference.

Suitable antifungal agents include, for example allylamines, such as terbinafine, naftifine and butenafine; and azoles, such as imidadazoles and triazoles, and the like. Imidazoles include ketoconazole, bifonazole, butoconazole, chlordantoin, chlormidazole, cloconazole, clotrimazole, econazole, enilconazole, fenticonazole, flutrimazole, isoconazole, lanoconazole, miconazole, neticonazole, omoconazole, oxiconazole nitrate, sertaconazole, sulconazole, and tioconazole. Triazoles include fluconazole, itraconazole, posaconazole, saperconazole, terconazole and voriconazole. Particularly preferred is the allylamine, terbinafine; the imidazole, ketoconazole; and the triazoles fluconazole, and itraconazole.

This invention as described is particularly applicable to terbinafine and its acid addition salts without limitation thereto. The practice of this invention using terbinafine is desired since increasing the topical bioavailability of this antifungal drug is useful in the treatment of onychomycosis of the toenails or fingernails. Beneficially, the dual action antifungal nail coat composition can shorten the total therapeutic period, avoid and eliminate systemic adverse events, and improve clinical efficacy because it is applied to the target site of the fungal infection.

Terbinafine is designated chemically as (E)-N-(6,6-dimethyl-2-hepten-4-ynyl)-N-methyl-1-naphthalene methanamine and has the following structural formula:

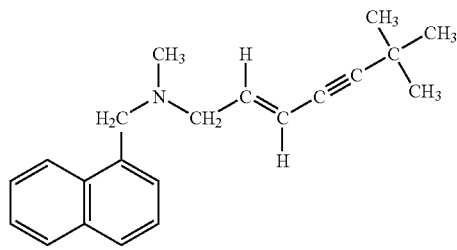

The term "terbinafine" as used herein includes the free base form of this compound as well as chemotherapeutically acceptable acid addition salts thereof. Suitable salt forms include hydrochloride, hydrogen fumarate or naphthaline-1, 5-disulphonate. For purposes of the present invention, the inorganic acid salt, terbinafine hydrochloride, is particularly preferred. Terbinafine hydrochloride is a synthetic antimycotic allylamine related to naftifine, and is the active ingredient (equivalent to 250 mg base) of a commercial antifungal medication sold under the name LAMISIL® (Novartis Pharmaceuticals Corporation) formulated in tablets for oral administration. The preparation of propenylamines, which includes terbinafine, is described in U.S. Pat. No. 4,755,534 and topical application dosage forms for pharmaceutical use reported therein are ointments or creams at concentrations of from 0.05 to 5, and 0.1 to 1 weight percent, in particular.

The present invention permits optimization of the clinical and mycological efficacy of terbinafine in a comprehensive management program based on topical treatment for ameliorating various severities of onychomycosis of fingernails and toenails as well as the surrounding skin where dermatophytes harbor. The comprehensive management program preferably comprises a daily regimen of topically applying a dual action antifungal nail coat composition as described below to ameliorate or prevent onychomycosis, and preferably includes removal of the unattached infected nail at least monthly.

The dual action antifungal nail coat composition embodiments can be formulated as a "one-coat" type composition or as a "two-coat" type composition. The term "one-coat type composition," as used herein, means that the antifungal nail coat composition contains a volatile carrier to assist in initially distributing the drug on contact with the nail and the surrounding skin, and then volatilize relatively quickly, (i.e., within a period in the range of about 0.5 to about 10 minutes), so that the hydrophilic polymer and substantially non-volatile permeation enhancer can provide a substantially uniform fungicidal film coat on the nail and adjacent skin tissue as a depot for the drug to provide ongoing amelioration or fungicidal prevention efficacy. The fungicidal film coat thus remains in contact with the nail until the nail coat is removed, such as by water rinsing or bathing. In this manner, an undesirable build-up of polymeric carrier films encountered by prior art antifungal nail lacquers is avoided.

A one-coat type composition is preferably applied at least once daily, as needed, and can be re-applied with or without an intervening water rinse.

In a one-coat type of antifungal nail composition, the amount of antifungal agent present usually is in the range of about 0.1 to about 20 weight percent, preferably in the range of about 0.5 to about 15 weight percent, and most preferably in the range of about 1 to about 5 weight percent.

The term "two-coat type antifungal nail composition," as used herein, refers to a two-part, dual action antifungal nail coat composition formulation, each of which is sequentially applied, at least once daily. Thus a two-coat type antifungal nail composition comprises: a first antifungal nail coat composition, which provides a fungicidal primer coat for relatively quick, substantially uniform, permeation of terbinafine into, across and onto the nail plate and the adjacent tissue area, and a second antifungal nail coat composition which subsequently provides a substantially uniform film depot coat over the fungicidal primer-coated nail to act as a nail-protective barrier and a depot for additional terbinafine which can be gradually released. Thus, the second antifungal nail composition is applied directly to the primer-coated nail with no intervening water rinse.

In a two-coat type embodiment of an antifungal nail coat composition, the amount of antifungal agent present in the respective first and second antifungal nail coat compositions can vary, but preferably, the weight ratio of antifungal agent in the second nail coat composition relative to that in the first nail coat composition is less than about one. Depending on the severity of the infection, the amount of antifungal agent in the first antifungal nail coat composition can vary in the range of about 0.1 to about 20 percent by weight of the total composition, and the amount of antifungal agent in the second nail coat composition may be an amount in the range of about 0.1 to about 15 percent by weight of the total composition.

A preferred first antifungal nail coat composition embodiment for a two-coat type composition is a substantially clear, colorless solution containing terbinafine at a concentration in the range of about 0.5 to about 20 weight percent, more preferably about 10 weight percent dissolved in a volatile, pharmaceutically acceptable carrier. The volatile carrier preferably is an alkanol having 2 to about 5 carbon atoms, such as ethanol, propanol, isopropanol, butanol, isobutanol, and the like. Ethanol is particularly preferred. The volatile carrier can also serve as a penetration enhancer.

A particularly preferred first antifungal nail coat composition comprises about 10 percent terbinafine in ethanol on a weight/weight basis. Preferably, the first antifungal nail coat composition wicks along the capillary system of and across the nail plate to reach and immobilize fungal spores in the nail plate and nail bed. A particularly preferred second antifungal nail coat composition for a two-coat composition embodiment preferably comprises terbinafine at a concentration in the range of about 0.1 to not more than about 10 weight percent, an effective film-forming amount of a hydrophilic film-forming polymer and a pharmaceutically acceptable, volatile carrier as described above as the remainder. The volatile carrier in the first and second compositions can be the same or different as desired.

The hydrophilic polymer may be a film-forming polymer comprising a vinylpyrrolidone monomer unit, including a homopolymer, (i.e., polyvinylpyrrolidone), a copolymer and a complex thereof, a gum, a resin, or the like. The term "copolymer" as used herein and in the appended claims means any polymer comprising two or more different monomer repeating units and includes polymers commonly referred to as "terpolymers," "tetrapolymers" and the like.

Exemplary film-forming polymers containing vinylpyrrolidone (VP) monomer units, are polyvinylpyrrolidone (PVP), sold in a range of viscosity grades, and varying weight average molecular weights in the range of about 8,000 to about 3,000,000 Daltons (PVP K homopolymer series). PVP is sold under the trade name KOLLIDON® CL by BASF Corporation. A USP grade of povidone (PVP) is preferred. Exemplary film-forming copolymers include vinylpyrrolidone/vinylaacetate (VA) copolymers available in a range of mole ratios of VP/VA such as the PVP/VA copolymer series sold by ISP, and the like. An exemplary VP complex is povidone-iodine (PVP-I).

The hydrophilic polymer preferably is a polyvinylpyrrolidone having a "K" value of about 30 (i.e., a weight average molecular weight in the range of about 45,000-60,000 Daltons.

Exemplary gums include agar gum, carrageenan gum, ghati gum, karaya gum, rhamson gum, xanthan gum and the like.

Exemplary resins include carbomer, a polyacrylic acid polymer lightly cross-linked with polyalkenyl polyether. It is commercially available from Noveon Inc. (Cleveland, Ohio) under the designation "CARBOPOL®." A particularly preferred grade of carbomer is that designated as "CARBOPOL® 940." Other polyacrylic acid polymers suitable for use are those commercially available under the designation "PEMULEN®" (Noveon Inc.) and POLYCARBOPHIL™ (A. H. Robbins Company, Inc., Richmond, Va.), is a polyacrylic acid cross-linked with divinyl glycol. The PEMULEN® polymers are copolymers of $C_{10}$ to $C_{30}$ alkyl acrylates and one or more monomers of acrylic acid, methacrylic acid or one of their simple esters cross-linked with an allyl ether of sucrose or an allyl ether of pentaerythritol.

There is no limitation on the form (i.e., liquid or powder) of hydrophilic film-forming polymer used, or the amount used as long as the nail coat composition can be easily applied to the nail and form a film thereon.

The present dual action antifungal nail coat composition can include one or more substantially non-volatile penetration enhancers, auxiliary anti-infectives, such as antibacterial agents, antiseptic agents, and the like, and mixtures thereof. In two-coat composition embodiments, one or more substantially non-volatile penetration enhancers can be included in either the first antifungal nail coat composition or the second antifungal nail coat composition or in both. The penetration enhancers in the antifungal nail coat compositions of this invention preferably enhance the penetration of the drug into the nail as well as the surrounding skin tissue area.

Among preferred skin penetration enhancers are ethanol, propylene glycol, glycerol, ethyl laurate, isopropyl palmitate, isopropyl myristate, laurocapram (AZONE®), dioxolanes (described in U.S. Pat. No. 4,861,764), macrocyclic ketones, 1-decyl-thiolthyl-2-pyrrolidone (HP-101), oxazolidones and biodegradable penetration enhancers (described in U.S. Pat. Nos. 4,980,378 and 5,082,866 to Wong et al. such as alkyl-2-(N,N-disubstituted amino) alkanoates (e.g., dodecyl-2-(N,N-dimethylamino) isopropionate (DDAIP)), N,N-disubstituted amino alkanol alkanoates) and mixtures thereof. Aliphatic and aromatic alcohols are primarily nail penetration enhancers.

The penetration enhancer)is present in an amount sufficient to enhance the penetration of the antifungal agent. The specific amount varies necessarily according to the desired release rate and the specific antifungal agent used. Generally, the penetration enhancer is present in an amount ranging from about 0.1 weight percent to about 25 weight percent, based on the total weight of the antifungal nail coat composition. Preferably, the penetration enhancer is present in an amount ranging from about 0.1 weight percent to about 10 weight percent, more preferably, in an amount ranging from about 0.5 weight percent to about 5 weight percent of the antifungal nail coat composition.

In general, suitable penetration enhancers can be chosen from those listed above, as well as aliphatic and aromatic alcohols, sulfoxides, fatty acids, fatty acid esters, polyols, amides, surfactants, terpenes, alkanones, organic acids and mixtures thereof. See generally Chattaraj, S. C. and Walker, R. B., Penetration Enhancer Classification, pp. 5-20 in Maibach, H. I., and Smith, H. E., (eds.), *Percutaneous Penetration Enhancers*, CRC Press, Inc., Boca Raton, Fla. (1995) and Büyüktimkin, N., et al., Chemical Means of Transdermal Drug Permeation Enhancement, in Ghosh, T. K., and Pfister, W. R. (eds.) *Transdermal and Topical Drug Delivery Systems*, Interpharm Press, Inc., Buffalo Grove, Ill. (1997).

Suitable alcohols include, without limitation, ethanol, propanol, butanol, pentanol, hexanol, octanol, nonanol, decanol, 2-butanol, 2-pentanol, benzyl alcohol, phenoxyethanol, caprylic alcohol, decyl alcohol, lauryl alcohol, 2-lauryl alcohol, myristyl alcohol, cetyl alcohol, stearyl alcohol, oleyl alcohol, linolyl alcohol, linolenyl alcohol and mixtures thereof. Volatile aliphatic alcohols having 2 to about 5 carbon atoms can provide a dual function of serving both as volatile carrier and penetration enhancer. The aromatic alcohols, such as benzyl alcohol, phenoxyethanol, and the like can provide a dual function of serving both as a substantially non-volatile, permeation enhancer and auxiliary anti-infective. Preferred alcohols are ethanol and benzyl alcohol.

Suitable sulfoxides include dimethylsulfoxide (DMSO), decylmethylsulfoxide, and mixtures thereof.

Suitable fatty acids include valeric, heptanoic, pelargonic, caproic, capric, lauric, myristic, stearic, oleic, linoleic, linolenic, caprylic, isovaleric, neopentanoic, neoheptanoic, neononanoic, trimethyl hexanoic, neodecanoic and isostearic acids, and mixtures thereof.

Suitable fatty acid esters include isopropyl n-butyrate, isopropyl n-hexanoate, isopropyl n-decanoate, isopropyl myristate, isopropyl palmitate, octyldodecyl myristate, ethyl acetate, butyl acetate, methyl acetate, methylvalerate, methylpropionate, diethyl sebacate, ethyl oleate, ethyl laurate and mixtures thereof. Suitable polyols include propylene glycol, polyethylene glycol, ethylene glycol, diethylene glycol, triethylene glycol, dipropylene glycol, glycerol, propanediol, sorbitol, dextrans, butanediol, pentanediol, hexanetriol, and mixtures thereof.

Suitable amides include urea, dimethylacetamide, diethyltoluamide, dimethylformamide, dimethyloctamide, dimethyldecamide, pyrrolidone derivatives, 1-alkyl-4-imidazolin-2-one, cyclic amides, hexamethylenelauramide and its derivatives, diethanolamine, triethanolamine and mixtures thereof. Suitable pyrrolidone derivatives include 1-methyl-2-pyrrolidone, 2-pyrrolidone, 1-lauryl-2-pyrrolidone, 1-lauryl- 4-carboxy-2-pyrrolidone, 1-methyl-4-carboxy-2-pyrrolidone, 1-hexyl-4-carboxy-2-pyrrolidone, 1-decylthioethyl-2-pyrrolidone (HP-101), N-cyclohexylpyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-dimethylaminopropylpyrrolidone, N-cocoylpyrrolidone, N-tallowylpyrrolidone, fatty acid esters of N-(2-hydroxymethyl)-2-pyrrolidone, and mixtures thereof. Suitable cyclic amides include, 1-dodecylazacycloheptan-2-one (laurocapram, AZONE®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethyloctyl)azacycloheptan-2-one, 1-geranylazacyclohexan-2-one, 1-geranylazacyclopentan-2,5-dione, 1-farnesylazacyclopentan-2-one, and mixtures thereof.

Suitable surfactants include anionic surfactants, cationic surfactants, nonionic surfactants, amphoteric surfactants, bile salts and lecithin. Suitable anionic surfactants include sodium laurate, sodium lauryl sulfate, and mixtures thereof. Suitable cationic surfactants include cetyltrimethylammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride, and mixtures thereof. Suitable nonionic surfactants include α-hydro-ω-hydroxypoly(oxyethylene)-poly(oxypropyl) poly(oxyethylene) block copolymers, polyoxyethylene ethers, polyoxyethylene sorbitan esters, polyethylene glycol esters of fatty alcohols, and mixtures thereof. Suitable α-hydro-ω-hydroxypoly(oxyethylene)-poly(oxypropyl) poly(oxyethylene) block copolymers include Poloxamers 182, 184, 231, and mixtures thereof. Suitable polyoxyethylene ethers include PEG-4 lauryl ether (BRIJ® 30), PEG-2 oleyl ether (BRIJ® 93), PEG-10 oleyl ether (BRIJ® 96), PEG-20 oleyl ether (BRIJ® 99), and mixtures thereof. Suitable polyoxyethylene sorbitan esters include the monolaurate (TWEEN® 20) the monopalmitate (TWEEN® 40), the monostearate (TWEEN® 60), the monooleate (TWEEN® 80), and mixtures thereof. Suitable polyethylene glycol esters of fatty acids include polyoxyethylene (8) monostearate (MYRJ® 45), polyoxyethylene (30) monostearate (MYRJ® 51), the polyoxyethylene (40) monostearate (MYRJ® 52), and mixtures thereof.

Suitable amphoteric surfactants include, without limitation thereto, lauramidopropyl betaine, cocamidopropyl betaine, lauryl betaine, cocobetaine, cocamidopropylhydroxysultaine, aminopropyl laurylglutamide, sodium cocoamphoacetate, sodium lauroamphoacetate, disodium lauroamphodiacetate, disodium cocoamphodiacetate, sodium cocoamphopropionate, disodium lauroamphodipropionate, disodium cocoamphodipropionate, sodium lauriminodipropionate, disodium cocoamphocarboxymethylhydroxypropylsulfate, and the like.

Suitable bile salts include sodium cholate, sodium salts of laurocholic, glycolic and desoxycholic acids, and mixtures thereof.

Suitable terpenes include D-limonene, α-pinene, β-enrene, α-terpineol, terpinen-4-ol, carvol, carvone, pulegone, piperitone, menthone, menthol, geraniol, cyclohexene oxide, limonene oxide, α-pinene oxide, cyclopentene oxide, 1,8-cineole, ylang ylang oil, anise oil, chenopodium oil, eucalyptus oil, and mixtures thereof. Suitable alkanones include N-heptane, N-octane, N-nonane, N-decane, N-undecane, N-dodecane, N-tridecane, N-tetradecane, N-hexadecane, and mixtures thereof. Suitable organic acids include citric acid, succinic acid, salicylic acid, salicylates (including the methyl, ethyl and propyl glycol derivatives), tartaric acid, and mixtures thereof.

A preferred, substantially non-volatile, penetration enhancer comprises an N,N-di($C_1$-$C_8$) alkylamino substituted, ($C_4$-$C_{18}$) alkyl ($C_2$-$C_{18}$) carboxylic ester or pharmaceutically acceptable acid addition salt thereof. As used herein, the term "($C_4$-$C_{18}$) alkyl ($C_2$-$C_{18}$) carboxylic ester" means an ester of a ($C_4$-$C_{18}$) alcohol and a ($C_2$-$C_{18}$) carboxylic acid. The term "N,N-di($C_1$-$C_8$) alkylamino substituted," in reference to a ($C_4$-$C_{18}$) alkyl ($C_2$-$C_{18}$) carboxylic ester means that either the alcohol portion or the carboxylic acid portion from which the ester is prepared bears an amino substituent $NR_xR_y$, wherein $R_x$ and $R_y$ are each independently a ($C_1$-$C_8$) alkyl group. Preferably $R_x$ and $R_y$ are both methyl groups.

Preferred are dodecyl-2-(N,N-dimethylamino) propionate (DDAIP); dodecyl-2-(N,N-dimethylamino)-acetate (DDAA); 1-(N,N-dimethylamino)-2-propyl dodecanoate (DAIPD); 1-(N,N-dimethylamino)-2-propyl myristate (DAIPM); 1-(N,N-dimethylamino)-2-propyl oleate (DAIPO); and pharmaceutically acceptable acid addition salts thereof.

A particularly preferred skin permeation enhancer is DDAIP, alone or in combination with an auxiliary permeation enhancer. DDAIP.HCl is available from Steroids, Ltd. (Chicago, Ill.) and Pisgah Laboratories (Pisgah Forest, N.C.). Particularly preferred is the hydrochloride of DDAIP (DDAIP.HCl). The preparation of DDAIP and crystalline acid addition, salts thereof is described in U.S. Pat. No. 6,118,020 to Büyüktimkin, et al., which is incorporated herein by reference. Long chain similar amino substituted, alkyl carboxylic esters can be synthesized from readily available compounds as described in U.S. Pat. No. 4,980,378 to Wong, et al., which is incorporated herein by reference to the extent that it is not inconsistent herewith.

The term "anti-infective agent" as used herein includes a topical antibacterial, antiseptic, or the like, that can augment the efficacy of the dual action antifungal nail coat composition. Suitable antibacterial agents include bacteriostatic preservatives, such as benzyl alcohol, phenoxyethanol, phenethylalcohol, iodopropynl butyl carbamate, paraben, and the like. Benzyl alcohol is particularly preferred, and when present can serve a dual purpose as penetration enhancer and anti-infective.

Suitable antiseptic agents include alcohol (i.e., ethanol, isopropanol), halogen containing compounds, (i.e., povidone-I, triclosan, and the like); quaternary ammonium compounds (i.e., benzethonium chloride, cetylpyridimum chloride, and the like).

Those skilled in the art will recognize that one or more of the foregoing ingredients can serve more than one function.

A preferred dual action, one-coat type antifungal nail coat composition embodiment comprises:

an effective fungicidal amount of an antifungal agent;

a permeation enhancing amount of a substantially non-volatile, permeation enhancer selected from the group consisting of an N,N-di($C_1$-$C_8$) alkylamino substituted, ($C_4$-$C_{18}$) alkyl ($C_2$-$C_{18}$) carboxylic ester or pharmaceutically acceptable acid addition salt thereof, a pharmaceutically acceptable alcohol, and mixtures thereof;

a film-forming amount of a hydrophilic polymer; and a pharmaceutically acceptable, volatile organic carrier.

Preferably, the one-coat antifungal nail coat composition is a substantially clear formulation.

A preferred dual action, one-coat type embodiment of antifungal nail coat composition comprises on a total composition weight basis:

antifungal agent in an amount in the range of about 0.1 to about 20 weight percent, more preferably in the range of about 0.5 to about 15 weight percent; most preferably in the range of about 1 to about 5 weight percent;

a substantially non-volatile permeation enhancer in a total amount in the range of about 0.1 to about 25 weight percent, more preferably in the range of about 1 to about 10 weight percent;

a hydrophilic film-forming polymer in an amount in the range of about 0.1 to about 5 weight percent, more preferably in the range of about 0.25 to about 1 weight percent; and the remainder comprising a pharmaceutically acceptable volatile organic carrier. A preferred volatile organic carrier is an aliphatic alcohol preferably present in an amount in the range of about 50 to about 99.5 weight percent, more preferably in the range of about 85 to about 99, based on a total composition weight basis.

A particularly preferred substantially clear, dual-action, one-coat type antifungal nail coat composition comprises on a total composition weight basis:

terbinafine hydrochloride present in an amount in the range of about 0.5 to about 10 weight percent, more preferably in the range of about 1 to about 5 weight percent;

DDAIP.HCl present in an amount in the range of about 0.1 to about 25 weight percent, more preferably in the range of about 0.1 to about 10 weight percent;

benzyl alcohol present in an amount in the range of about 0.1 to about 10 weight percent, more preferably in the range of about 0.5 to about 1.5 weight percent;

polyvinylpyrrolidone present in an amount in the range of about 0.1 to about 5 weight percent, more preferably in the range of about 0.25 to about 1 weight percent; and the remainder being ethanol.

In a two-coat type embodiment utilizing first and second antifungal nail coat compositions, the second antifungal nail coat composition preferably is formulated so that the film coat deposited on fingernails is substantially more resistant to ready removal with water than the primer film coat deposited on toenails.

A particularly preferred, two-coat type dual action antifungal nail coat composition comprises, in the first or primer antifungal nail coat composition, on a total composition weight basis, about 10 weight percent terbinafine in ethanol, and in the second antifungal nail coat composition preferably not more than about 5 weight percent terbinafine. A presently preferred second or depot antifungal nail coat composition comprises about 20 parts by weight polyvinylpyrrolidone, about 3 parts by weight terbinafine, and about 47 parts by weight ethanol.

Based on in vitro test studies using human nail clippings, it was found that terbinafine applied as a 10% solution in ethanol can diffuse across a nail membrane and, in a period of about one hour, can reach a concentration above the minimum inhibition concentration (MIC) for fungi.

Fungal infection of a toenail or fingernail may be ameliorated or prevented by a one-coat method, or a two-coat method as described below.

A one-coat type dual action antifungal nail coat composition can be applied to provide a substantially uniform fungicidal coating on a fungally susceptible or infected nail and adjacent skin tissue and maintained in contact therewith for a period of at least about 0.5 hour. In a one-coat method, the nail coat composition can be removed subsequently by rinsing with water. In a multiple-coat method, the composition can be re-applied at least twice with or without an intervening water rinse. The nail coat composition is preferably applied in a daily regimen for a period sufficient to achieve fungicidal efficacy.

A two-coat type dual action antifungal nail coat composition of this invention can be applied by the following multiple-coat method.

(1) A first antifungal nail coat composition containing an effective fungicidal amount of antifungal agent is applied at least once to an infected fingernail or toenail, and surrounding skin area, to provide an active fungicidal primer coat;

(2) The active fungicidal primer coat is allowed to substantially dry for about 10 minutes or until the fungicidal primer-coated nail is substantially dry to the touch; and then (3) The substantially dry fungicidal primer-coated nail is coated with a sufficient fungicidal amount of a second antifungal nail coat composition to provide a fungicidal film coat thereon for further release of antifungal agent to the nail.

In the initial period of a fungicidal regimen with a two-coat type dual action antifungal nail coat composition, multiple applications of the first antifungal nail coat composition can be applied, by performing sequential steps (1) and (2) at least twice before performing step (3) to further optimize the bioavailability of antifungal agent.

The methods of this invention are preferably practiced daily until new nail growth is visibly free of fungal infection.

It was found that the practice of a two-coat method of this invention with terbinafine extended the residence time of the terbinafine applied from the first antifungal nail coat composition, that the hydrophilic polymer film coat of the second antifungal nail coat composition promoted the formation of an internal and external barrier membrane, and that a high efficacy in ameliorating or preventing onychomycosis within a relatively short period of about four weeks was achieved.

The nail coat compositions of the present invention can be applied to the nail by any convenient method, such as by brushing or spraying. Preferably the applied composition is substantially dry to the touch within a period in the range of about 0.5 to about 10 minutes, more preferably within a period in the range of about one to about five minutes, depending upon the amount of volatile organic carrier present.

The fungicidal nail coat compositions may be provided in kit form with instructional indicia included therein for use. The first and second antifungal coat compositions of a two-coat dual action, antifungal nail coat composition may be individually packaged in similar or dissimilar shaped packages or are color coded to visibly distinguish the first and second compositions from one another to aid the user in following the therapeutical order of application.

Instructional indicia includes, without limitation, printed media, aural media, visual aids, electronic media or a combination thereof which inform and instruct the user. Printed media includes, but is not limited to, labels, pamphlets, books, flyers and the like. Aural media includes, but is not limited to, tape recordings, audio compact disks, records, and the like. Visual aids include, but are not limited, to photographs, slides, movies, videos, DVDs, and the like. Electronic media includes all forms of electronic data storage media, such as, but not limited to, diskettes, interactive CD-ROMs, interactive DVDs, and the like.

The following examples are intended to illustrate, but not limit, the present invention.

EXAMPLE 1

The preliminary efficacy and safety of terbinafine hydrochloride in a two-coat type dual action, antifungal nail coat composition and method of this invention was studied with patients having toenail and/or fingernail fungal infection. The patients participated in an open label, single hospital pilot clinical study over a period of three months.

Up to 20 patients were selected assessed as having mild to severe onychomycosis, as measured by using a scale of infection, based on nail plate separation from the nail bed, hyperkeratosis, and discoloration. The extent of onychomycosis, hyperkeratosis, and discoloration were assessed using the following scale ratings:

Onychomycosis
0=absence of separation of nail plate from nail bed.
1=≦50% separation of nail plate.
2=>50% but ≦75% separation of nail plate.
3=>75% separation of nail plate.
Hyperkeratosis
0=absence of subungual debris.
2=thickening of ≦50% of the subungual region.
2=>505 but ≦75% thickening of the subungual region.
3=>75% thickening of the subungual region.
Discoloration
0=absence of any unusual coloration (white, yellow, etc.) of the nail plate.
1=discoloration extending to ≦50% of the nail plate.
2=discoloration extending to >50% but ≦75% of the nail plate.
3=discoloration extending to >75% of the nail plate.

For inclusion in the study, the criteria were: onychomycosis patients between the ages of 18-70 years, having a nail involvement of at least 25% of the whole nail surface that included any destroyed or missing part of the nail plate. Onychomycosis of the finger nail or toenail was confirmed as follows by KOH staining microscopic examination and fungal culture.

The nail plate and hard debris were softened by leaving the fragments, along with several drops of potassium hydroxide (25% KOH with 5% glycerine), in a watch glass covered with a petri dish for 24 hours. Light microscope was used for the fungal examination. The small fragments of scale were placed on a microscope slide and a coverslip was applied. The preparation was studied carefully at low power. Dermatophytes appear as translucent branching, rod-shaped filaments of uniform width. If the presence of hyphae is confirmed by examination with the 40× objective, the test result is judged as positive.

Fungal culture was carried out using the standard culture medium, Sabouraud's agar, (agar 18 g, peptone 10 g, glucose 40 g, distilled water 1000 ml). Most medically important fungi are grown aerobically on this culture medium over an incubation period of about 24 hours to about 48 hours at a temperature of about 28° C.

The criteria for exclusion from the study were: onychomycosis caused by molds (*Candida* sp.); hypersensitivity to terbinafine; abnormal liver function (twice the upper limit value); receipt of topical treatment within 2 weeks or oral treatment within two months; concurrent treatment with H-blockers, antacid, rifampin, phenobarbital, phenytoin, carbamazepine, terfenadine (e.g. SELDANE™) or digoxin; use of any investigational drugs with one month; psoriasis or history of psoriasis; serious concurrent disease that might influence the trial; and pregnant women or nursing mothers.

Twenty patients (six females, 14 males) between the ages of 35-59 years, with an average age of 46 years, met the inclusion criteria. Of these 20 subjects, 17 completed 12 weeks of treatment. At the start of the study, the extent of onychomycosis was assessed as mild (i.e., ≦40% infected nail) for 15%, and as severe (i.e., >40% infected nail) for the remaining 85% of the 20 patients. Of the 20 patients, 45% of the patients had separation of nail plate; 45% had hyperkeratosis; and 10% had discoloration.

The primary efficacy criteria were mycological cure based on achieving a negative KOH staining microscopic examination and a negative fungal culture.

The secondary efficacy criteria were the physicians's assessment of the mycological cure and clinical efficacy. Clinical efficacy evaluation was assessed as follows: "Cleared" (i.e., no signs of mycosis, without residual nail deformity, no requirement for further therapy); "Markedly Improved" (i.e., minimal nail involvement with significantly decreased signs of mycosis; and "Slightly to Moderately Improved" (i.e., slight to moderate reduction in extent of nail involvement and signs of mycosis).

After the completion of the study, the clinical safety and efficacy of administration were analyzed by investigators based on adverse events, KOH staining microscopic examination, fungal culture, clinical efficacy assessment (i.e., planimetric measurement of the involved area, photographic comparison of new nail growth, and reduction in extent of nail involvement) and the physician's global evaluation.

The primary safety parameters included adverse events, vital signs, clinical laboratory tests, physical examinations, and electrocardiograms (ECG).

The patients assigned to the study were each provided with two bottles having brush applicators, each bottle containing nail coat composition (about 20 grams in each bottle), and identified as "A" and "B". Bottle "A" contained terbinafine hydrochloride 10% (weight/weight) in ethanol. Bottle "B" contained 20 parts by weight polyvinylpyrrolidone (PVP, KOLLIDON® 30, weight average molecular weight in the range of about 45,000 -60,000 Daltons), 3 parts by weight terbinafine hydrochloride, and 47 parts by weight ethanol.

The patients were instructed to cleanse their feet or hands by using warm water, and cut or clean infected nails as much as possible, but not to file the nails. The patients were also instructed to apply the antifungal nail coat composition on the infected nail directly once each night substantially immediately after washing their feet.

The patients were instructed to first apply Solution A with the brush, let Solution A dry, and then apply Solution B with the brush and let Solution B dry. There were no limitations to avoid wetting or washing their feet. The coating was easy to wash off before re-applying the dual action antifungal nail coat composition. The patients were instructed that, after washing off the coating, the patient re-apply the antifungal nail coat composition right away. The doctors encouraged the patients to use the antifungal nail coat composition on a daily basis, especially for the first month.

The efficacy, based on primary efficacy (mycological cure), clinical efficacy (appearance of the new nail, disappearance of signs and symptoms), and total efficacy (i.e., both mycological evaluation and clinical evaluation assessments) at the end of the first, second and third month of the study period is summarized in Table 1.

TABLE 1

|  | Month 1 | | Month 2 | | Month 3 | |
| --- | --- | --- | --- | --- | --- | --- |
|  | Patients | % | Patients | % | Patients | % |
| Evaluated | 18 | 100 | 17 | 100 | 17 | 100 |
| Primary Efficacy | 7 | 38.9 | 8 | 47.1 | 9 | 52.9 |
| Clinical Efficacy | 6 | 33.3 | 10 | 58.8 | 16 | 94.1 |
| Total Efficacy | 7 | 38.9 | 8 | 47.1 | 9 | 52.9 |

As shown in Table 1, based on the assessed change in nail involvement, change in signs of fungal infection, and new nail growth, the clinical efficacy (including patients rated as "slightly to moderately improved," "markedly improved," and "cleared") at the end of the first, second, and third month of treatment, was 33.3%, 58.8% and 94.1%, respectively.

As shown in Table 2, the number of patients initially assessed as having severe onychomycosis decreased at the end of the first, second, and third month of the study period, and concurrently, the number of patients assessed as having mild onychomycosis increased.

TABLE 2

| Onychomycosis | Month 0 | | Month 1 | | Month 2 | | Month 3 | |
|---|---|---|---|---|---|---|---|---|
| | Patients | % | Patients | % | Patients | % | Patients | % |
| Evaluated | 20 | 100 | 18 | 100 | 17 | 100 | 17 | 100 |
| Mild ($\leq$40%) | 3 | 15 | 4 | 22.2 | 4 | 23.5 | 6 | 35.3 |
| Severe ($\geq$40%) | 17 | 85 | 14 | 77.8 | 13 | 76.5 | 11 | 64.7 |

One patient having "mild" onychomycosis and one patient having "severe" onychomycosis were judged as showing significant improvement at the end of the third month.

During the study period, the patients also maintained a diary from which the patient's experiences of any adverse events were recorded. No adverse events were reported by any of the patients during the study period.

It is recognized that new nail growth takes time. The nail reportedly grows continuously at the rate of 3-4 millimeters (mm) a month (0.112 to 0.132 mm a day), so some 4.5-5 months are required for a complete renewal of the nail. It is also recognized that the speed of nail growth differs between individuals as well as age groups (nail growth being more rapid in the young), and that certain health disorders and medications can upset the rate of growth. Thus, mycological evaluation was judged as the most proper objective primary efficacy criteria to best predict full future clinical efficacy. The efficacy of the two-coat type dual action antifungal nail composition within the short-term study period as judged safe and effective for ameliorating onychomycosis of varying intensity.

EXAMPLE 2

The uptake of antifungal agent by a nail substrate was evaluated in vitro using human nail clippings collected from one individual. The nail clippings were cleaned and extracted with anhydrous ethyl alcohol for several days before applying the antifungal agent, terbinafine hydrochloride.

About 15 mL of four antifungal containing solutions each were prepared comprising the following indicated amount, on a total composition volume basis, terbinafine hydrochloride, volatile organic carrier (ethanol), film-forming hydrophilic polymer (polyvinylpyrrolidone (PVP)), or penetration enhancer dodecyl-2-(N,N-dimethylamino) isopropionate hydrochloride (DDAIP.HCl)).

Solution A. 10 weight percent terbinafine hydrochloride in anhydrous ethyl alcohol.

Solution B. 10 weight percent terbinafine hydrochloride and 10 weight percent PVP (KOLLIDON® 30, BASF) in anhydrous ethyl alcohol.

Solution C. 10 weight percent terbinafine hydrochloride and 0.5 weight percent DDAIP.HCl in anhydrous ethyl alcohol.

Solution D. 10 weight percent terbinafine hydrochloride and 1 weight percent DDAIP.HCl in anhydrous ethyl alcohol.

The nail clippings were separately immersed in about 5 mL of each of solution A, B, C, and D (solid:liquid ratio of about 1:10), and the uptake of terbinafine was determined by measuring the concentration of terbinafine in the solution as a function of time over a period starting from immersion to about 24 hours. Measurement was made using High Performance Liquid Chromatography (HPLC) technique using a Waters Alliance HPLC. (Waters Symmetry C18, 3.5 nm 4.2× 75 mm column was equipped for the separations, UV 224 nm for detection, flow rate 1.5 mL/min., injection 20 μL). The buffer was composed of two parts triethylamine and 1000 parts of deionized water and the pH was adjusted to pH 7 with phosphoric acid. The mobile phase composition was 25 parts of buffer and 75 parts acetonitrile.

As shown graphically in FIG. 1, an initially fast decrease in the solution concentration of terbinafine was observed in all cases, which gradually approached equilibrium after about five hours, remaining substantially unchanged up to 24 hours, indicating that saturation had been reached. Uptake from Solution A reached equilibrium in less than about one hour, somewhat sooner than from Solutions B, C or D. In all cases, the average amount of terbinafine uptake was judged to be about 5.2 mg/100 mg nail or about 5.2% on a nail weight basis.

Figure 2:
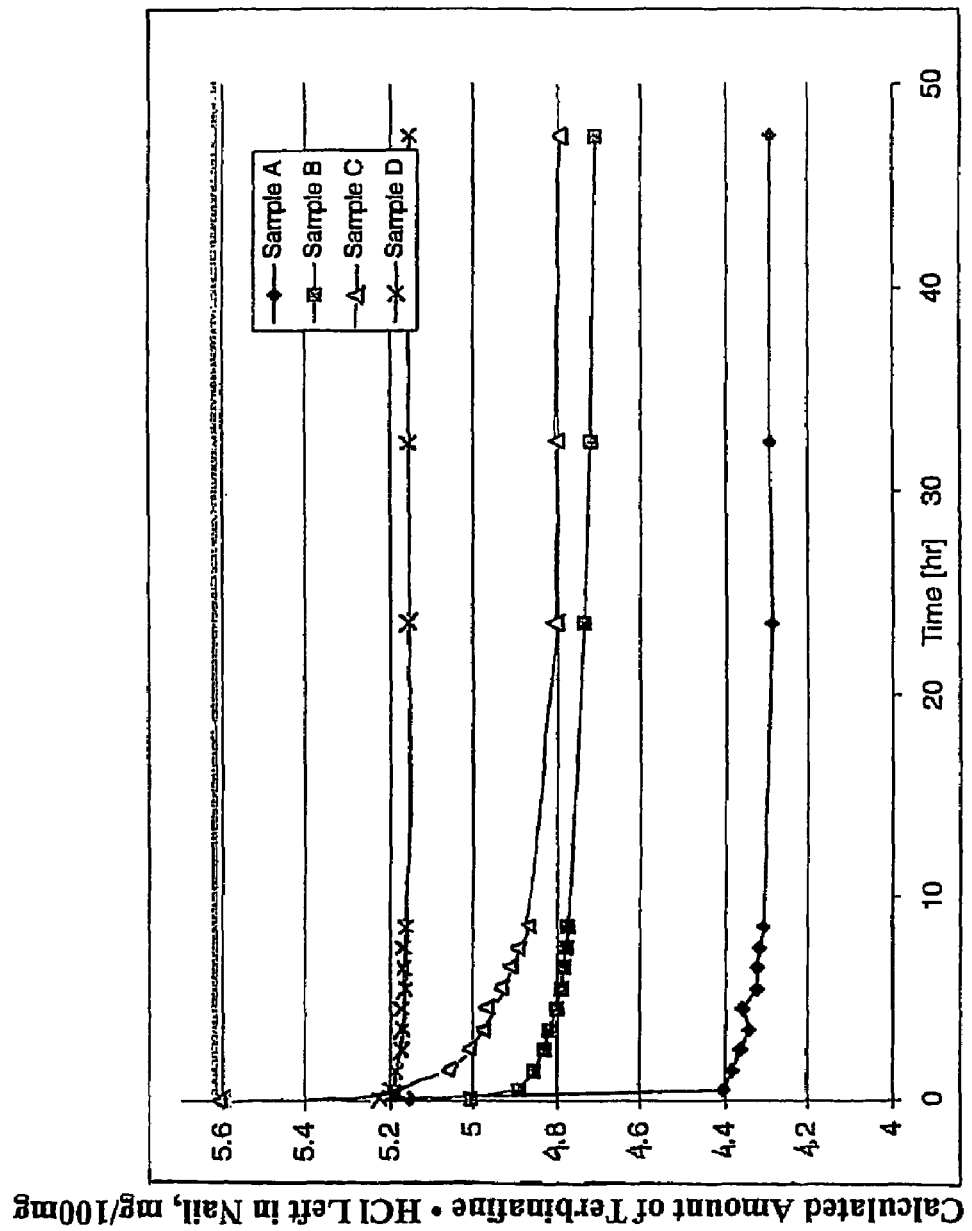
FIG. 2 is a graphical representation of terbinafine release from the human nail clippings of the selected individual of FIG. 1 expressed as a calculated amount of terbinafine hydrochloride remaining in the nail clippings as a function of time, wherein Sample A was previously treated with Solution A, Sample B was previously treated with Solution B, Sample C was previously treated with Solution C, and Sample D was previously treated with Solution D.

The terbinafine-treated nail clippings were then separately recovered from each test solution and rinsed with 10 mL of ethyl alcohol to remove antifungal liquid from the surface cavity. The rinsed nail clippings from each test were then separately immersed in another 5 mL portion of anhydrous ethyl alcohol to assess the rate of terbinafine release from the nail structure, by determining the concentration of terbinafine hydrochloride released as a function of time using the HPLC technique described above. The amount of terbinafine hydrochloride initially released from the nail, based on release measurements over a period of about 48 hours, was greater from nail treated with Solution A, than from nail treated with Solution B, C, or D. As shown graphically in FIG. 2, the amount of terbinafine hydrochloride retained in the nail reached equilibrium in a period of about 10 hours. The order of efficacy of treatment was Solution D>Solution C>Solution B>Solution A.

Figure 3:
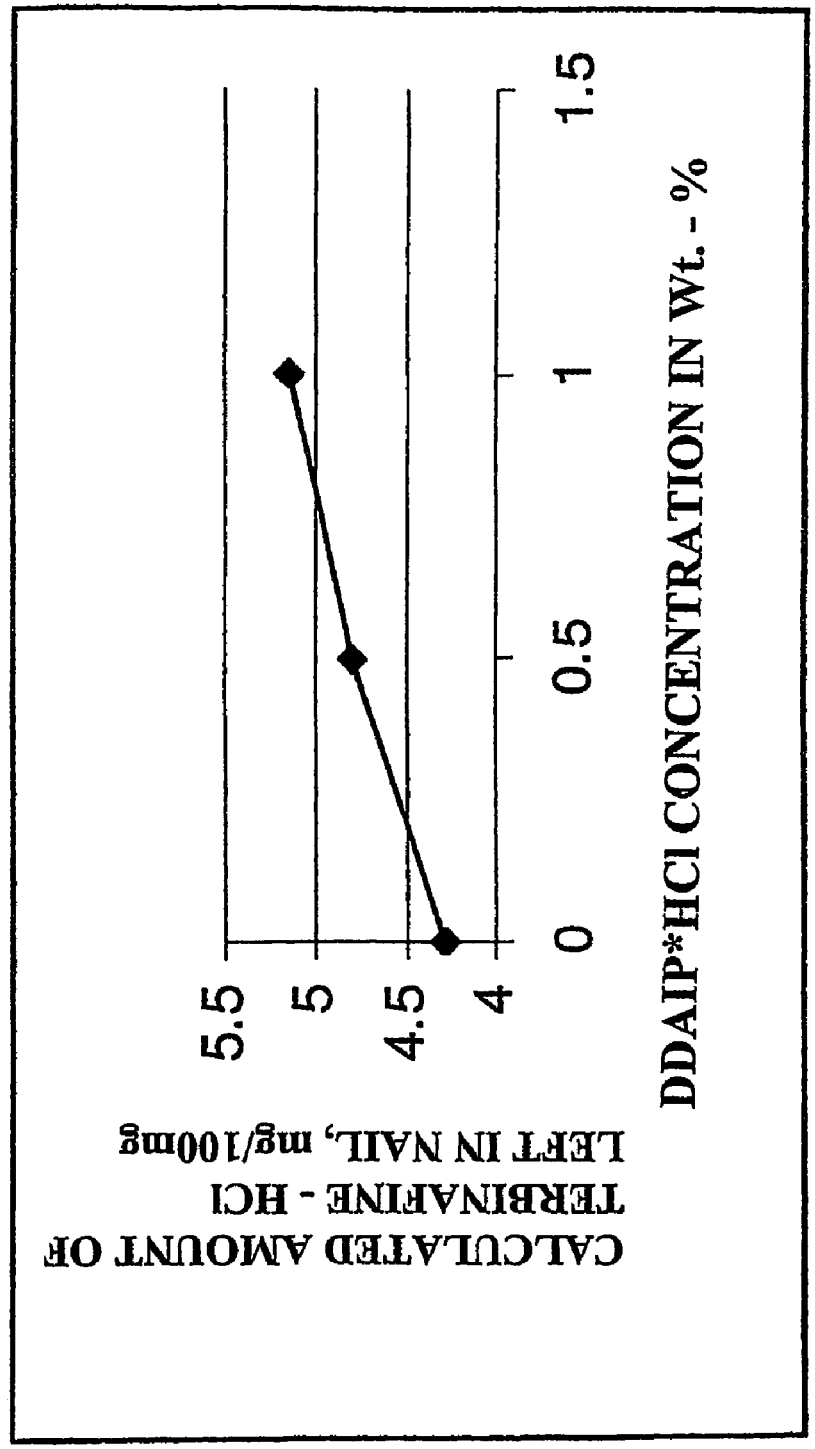
FIG. 3 is a graphical representation of the calculated amount of terbinafine hydrochloride retained in human nail clippings as a function of DDAIP.HCl concentration in a solution of terbinafine hydrochloride in anhydrous ethanol.

FIG. 3 graphically shows the retention of terbinafine hydrochloride update in the nails treated with Solutions C and D. The data indicated that the film-forming polymer in Solution B, and the penetration enhancer in Solutions C and D, contributed beneficially to increasing the residence time of terbinafine in the nail.

EXAMPLE 3

The permeation of terbinafine hydrochloride by human nail clippings as a function of time was compared using Solution A and C, prepared as in Example 2. Nail clippings having a substantially similar dry thickness (+/−5%) were selected. A selected nail clipping was anchored by being placed between two open metal frames, a sealant material was placed between the rim of the frame and the edge of the nail, and the edges of the nail were then compressed to stabilize the nail and provide a nail holder. The nail holder thus had an opening for permeation and was sealed against leakage when the anchored nail was placed in a horizontal Franz diffusion cell as a permeable membrane. The volume capacity of each of the donor cell and receiving cell was 3 mL, and the permeation area of about 78.5 square mm. The donor solution was the antifungal solution (Solution A or Solution C) and the receiver solution was anhydrous ethyl alcohol. The receiver solution was sampled periodically over a period of up to about 100 hours, and analyzed by HPLC, as in Example 2.

Figure 4:
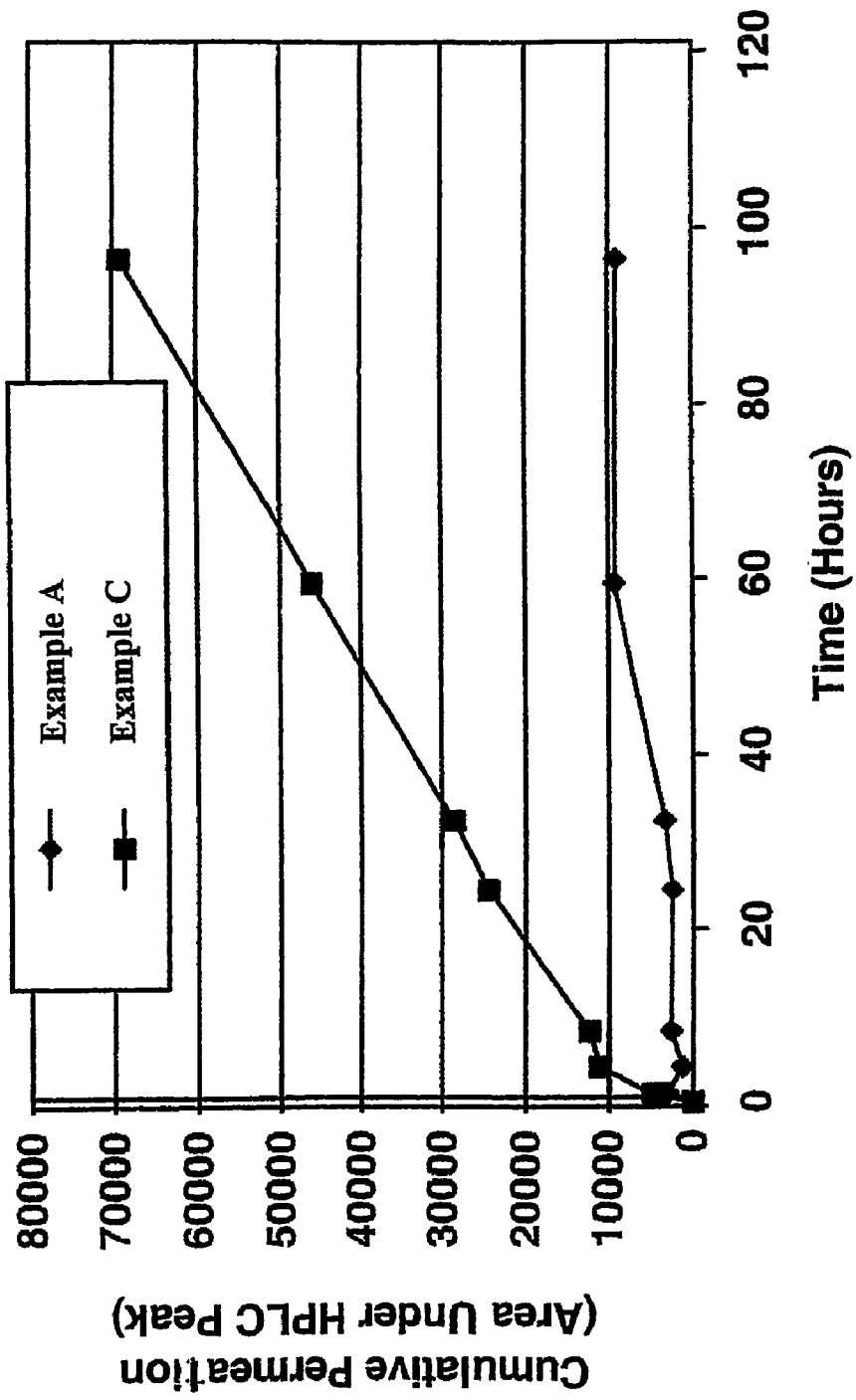
FIG. 4 is a graphical representation of the permeation of terbinafine hydrochloride in human nail clippings as a function of time from a 10 weight percent solution of terbinafine hydrochloride in anhydrous ethanol and from a 10 weight percent solution of terbinafine hydrochloride in anhydrous ethanol and also containing 0.5 weight percent DDAIP.HCl.

The cumulative permeation of terbinafine hydrochloride in the receiver is graphically shown in FIG. 4, and indicates an enhanced permeation of terbinafine hydrochloride through the nail from Solution C containing 10% terbinafine hydrochloride and 0.5% DDAIP.HCl over that of Solution A containing 10% terbinafine hydrochloride in anhydrous ethyl alcohol.

EXAMPLE 4

This example illustrates formulations for one-coat type dual action, antifungal nail coat compositions, (A), (B), (C), (D) and (E).

TABLE 3

| INGREDIENT | WEIGHT PERCENT | | | | |
|---|---|---|---|---|---|
| | (A) | (B) | (C) | (D) | (E) |
| Terbinafine•HCl | 1 | 5 | 10 | 1 | 1 |
| DDAIP•HCl | 0.5 | 0.5 | 0.5 | 2.5 | 5 |
| PVP, USP | 0.5 | 0.5 | 0.5 | 0.5 | 0.5 |
| Benzyl alcohol | 0.75 | 0.75 | 0.75 | 0.75 | 0.75 |
| Ethanol to 100% | q.s. | q.s. | q.s. | q.s. | q.s. | q.s. = quantity sufficient

EXAMPLE 5

This example illustrates, in a recognized guinea pig model of dermatophytosis caused by *Trichophyton mentagrophytes* (*T. mentagrophytes*) (ATCC 24953), the in vivo clinical and fungicidal efficacy of one-coat type dual action, antifungal nail coat compositions containing varying amounts of terbinafine hydrochloride and of penetration enhancer, DDAIP.HCl. Ten compositions were prepared having the amounts indicated in Table 4.

TABLE 4

| | Weight Percent Ingredient | | | | |
|---|---|---|---|---|---|
| Example | Terbinafine HCl | DDAIP•HCl | PVP, USP | Benzyl Alcohol | Ethanol to 100% |
| 5(A) (control) | None | None | 0.5 | 0.75 | q.s. |
| 5(B) | None | 0.5 | 0.5 | 0.75 | q.s. |
| 5(C) | 1 | None | 0.5 | 0.75 | q.s. |
| 5(D) | 5 | None | 0.5 | 0.75 | q.s. |
| 5(E) | 10 | None | 0.5 | 0.75 | q.s. |
| 5(F) | 1 | 0.5 | 0.5 | 0.75 | q.s. |
| 5(G) | 1 | 2.5 | 0.5 | 0.75 | q.s. |
| 5(H) | 1 | 5 | 0.5 | 0.75 | q.s. |
| 5(I) | 5 | 0.5 | 0.5 | 0.75 | q.s. |
| 5(J) | 10 | 0.5 | 0.5 | 0.75 | q.s. |

The procedures of the in vivo evaluation protocol used were in compliance with the Animal Welfare Act, the Guide for the Care and Use of Laboratory Animals, and the Office of Laboratory Animal Welfare. The protocol also was approved by the Institutional Animal Care and Use Committee (IACUC), and the IACUC Guidelines were followed. The evaluation was carried out at the Center for Medical Mycology and Mycology Reference Laboratory of Case Western Reserve University, Cleveland, Ohio.

Male albino Guinea-Pigs Harlan-Sprague-Dawley (San Diego, Calif.) having a body weight of about 400 to about 450 grams were acclimated for a minimum of five days prior to use. The environmental controls for the animal room were set to maintain a temperature in the range of about 16 to about 22° C., a relative humidity in the range of about 30 to about 70%, and a 12 hour light/12 hour dark cycle. Guinea pigs are naturally susceptible to dermatophyte infection and need no special manipulation, such as immunosuppression.

Each test guinea pig was anesthetized with an intramuscular (IM) injection of 0.1 ml of an anesthetic cocktail of xylazine, ketamine and acepromazine (3:3:1 by volume). Using an electric shaver, hair was clipped on the left side of the guinea pig's back. A closer shave was given with a safety razor. Using a stencil, a shaved skin area of about 2.5×2.5 cm$^2$ square was marked in quadrants, and the marked skin area was abraded with sterile fine grit sandpaper. The guinea pig was then infected topically by thoroughly rubbing onto the abraded skin a cell suspension of *T. mentagrophytes*, (ATCC 24953).

The *T. mentagrophytes* suspension was prepared by sub-culturing *T. mentagrophytes* (from frozen stock) on Potato Dextrose Agar (PDA) (Difco Laboratories) plates and incubating the plates at a temperature of about 30° C. for a period of about five to about seven days. The colonies were scraped from the plate using sterile saline solution (NaCl 0.85%). After washing three times with sterile saline solution, the conidia were re-suspended in sterile saline solution. A ten-fold dilution of conidia suspension was prepared and counted using a hemacytometer. A working suspension of conidia was prepared at a final concentration of 1×10$^7$ Colony Forming Units (CFU) per 100 microliters normal saline solution. The inoculum counts of the ten-fold dilution of *T. mentagrophytes* working conidial suspension was checked by plating the suspension onto Sabouraud Dextrose Agar (Difco Laboratories) media, incubating the plate at a temperature of about 30° C. for a period of about three to about four days, and then determining the colony counts.

Three days after the inoculation and infection with the dermatophyte, the guinea pigs were each treated, once daily for a period of seven days, with 0.1 mL/application of one of the selected nail coat compositions, 5(A-J), listed in Table 4. Three days after completion of the seven-day test period, mycological and clinical efficacy was examined.

Mycological efficacy was examined by removing hair samples with a sterile forceps from four quadrants, (10 representative hairs per quadrant). The hair samples were planted in a corresponding quadrant on a Potato Dextrose Agar plate and incubated at a temperature of about 30° C. for about two days. Following the two-day incubation period, the fungal growth at the hair root was examined under a stereo-microscope. The effectiveness of a test composition in reducing the number of mycologically positive hair samples per treated animal group was expressed as percentage efficacy relative to the untreated control group of animals using the following formula: % efficacy=100−(T×100/K), where T=positive hair in the test group and K=positive hair in the untreated control group.

Four guinea pigs were tested with the composition of Ex. 5(A) as a placebo (vehicle control) group (Group 1), five guinea pigs were tested with each one of the example formulations (Exs. 5(B-J) shown in Table 4, (identified as Groups 2-10 respectively), and one group of four guinea pigs was maintained as an infected control group (Group 11).

The hairs from the infected, control guinea pigs (Group 11) showed growth of fungal filaments indicating invasion of the hair roots. Substantially similar invasion of the hair roots was noted in the infected guinea pigs treated with placebo (Group 1) and with the drug-free composition of Ex. 5(B) (Group 2). All of the compositions containing terbinafine HCl, Exs. 5(C-J), had mycological efficacy as demonstrated by the absence of fungal elements in the hair.

Clinical efficacy was assessed by examining local changes in the appearance of the skin and regrowth of hair at the test sites, using the following numerical score criteria: 0=no lesions; 1=few slightly erythematous places on the skin; 2=well defined redness, swelling with bristling hairs; 3=large areas of marked redness incrustation, scaling, bald patches, ulcerated in places; 4=partial damage to the integument and loss of hair; and 5=extensive damage to the integument and complete loss of hair at the site of infection. The assessment of clinical evaluation in the change of scores per treated animal group was expressed as a percentage relative to the untreated control group of animals using the following formula: % efficacy=100−(T×100/K), where T=scores in the test group and K=scores in the untreated control group.

The infected control guinea pigs (Group 11) showed patches of hair loss and readily visible ulcerated or scaly skin. Substantially similar lesions were noted in the Group 1 guinea pigs treated with the placebo, Ex. 5(A), and the Group 2 guinea pigs treated with the drug-free composition, Ex. 5(B). All of the terbinafine-containing compositions, Exs. 5(C-J) had clinical efficacy, based on an improved appearance of the skin as demonstrated by healthier skin and regrowth of hair in the Groups 3-10 guinea pigs compared to that of guinea pigs treated with the placebo (vehicle) control and drug-free composition, Exs. 5(A-B). Clinical efficacy was judged optimized at a drug concentration of about 1 weight % (Ex. 5(C)) and at a DDAIP penetration enhancer concentration of about 0.5 weight % (Ex. 5(F)), because increasing the drug content or increasing the penetration enhancer content did not provide a further beneficial increase in clinical efficacy.

At the end of the study, all surviving animals were sacrificed by an intravenous injection of a euthanasia solution and disposed to the Animal Resource Center for incineration.

EXAMPLE 6

This example illustrates in vitro the permeability of a one-coat type dual action, antifungal nail coat composition containing terbinafine hydrochloride through hard keratin, using an animal hoof keratin model (horse hoof) and an agar plate diffusion assay.

Three discs, (I, II, and III) were cut from horse hoof keratin to a thickness in the range of about 0.5 to about 1 millimeter (mm) (Disc I); a thickness in the range of about 1.1 to about 1.5 mm (Disc II); and thickness in the range of about 1.6 to about 2 millimeter (mm) (Disc III). The side edges and one face of each disc was coated with Vaseline to prevent seepage of the antifungal drug during agar diffusion evaluation leaving the opposing face exposed.

In one diffusion assay evaluation, three separate antifungal coat solutions, 6(A), 6(B), 6(C), were prepared, respectively containing 25 mg/ml, 0.5 mg/ml, and 1 mg/ml amounts of terbinafine hydrochloride in dimethylsulfoxide (DMSO). Each antifungal coat solution was applied to the exposed face of each selected hoof disc (I, II, and III). The antifungally-coated face of the hoof disc was then placed in contact with an agar plate seeded with a lawn of conidial suspension of *T. mentagrophytes* (ATCC 24953) at a concentration of $5\times10^5$, and incubated for a period of about eight hours. The zone of inhibition (diameter of area remaining clear, i.e., lacking growth) was then measured in millimeters (mm).

The results showed that, at all concentrations of terbinafine hydrochloride, diffusion took place through the hoof and that the permeate retained bioactivity. The measured zones of inhibition were generally inversely proportional in diameter to the thickness of the hoof disc. Hoof disc II having a thickness in the range of about 1.1 to about 1.5 mm is judged similar to the thickness of human nails.

EXAMPLE 7

This example simulates the clinical use of a one-coat type dual action, antifungal nail coat composition on human nails using the horse hoof model described in Example 6.

The general procedure for simulating clinical use is as follows: The horse hoof is cleaned and washed three times with buffer. Sections of horse hoof having a thickness of about 100 micrometers are cut using an Arbor blade and are sterilized by autoclaving. Individual hoof sections are then coated with a selected nail coat composition containing the amount of terbinafine hydrochloride and penetration enhancer shown in Compositions 7(A-H) of Table 5, and left in contact with the nail coat composition. For comparison, sections of horse hoof are similarly contacted with a commercial topical nail lacquer, PENLAC™ containing the synthetic antifungal, ciclopirox, (Ex. 7(I)). The treated hoof sections are then each placed on an agar plate seeded with a lawn of conidial suspension of *T. mentagrophytes* (ATCC 24953) at a concentration of $5\times10^5$, and incubated for a period of about four days at a temperature of about 35° C. The zone of inhibition was then measured.

TABLE 5

| | Weight Percent Ingredient | | | | |
|---|---|---|---|---|---|
| Example | Terbinafine HCl | DDAIP•HCl | PVP, USP | Benzyl Alcohol | Ethanol to 100% |
| 7(A) | 1 | None | 0.5 | 0.75 | q.s. |
| 7(B) | 5 | None | 0.5 | 0.75 | q.s. |
| 7(C) | 10 | None | 0.5 | 0.75 | q.s. |
| 7(D) | 1 | 0.5 | 0.5 | 0.75 | q.s. |
| 7(E) | 1 | 2.5 | 0.5 | 0.75 | q.s. |
| 7(F) | 1 | 5 | 0.5 | 0.75 | q.s. |

TABLE 5-continued

| | Weight Percent Ingredient | | | | |
|---|---|---|---|---|---|
| Example | Terbinafine HCl | DDAIP•HCl | PVP, USP | Benzyl Alcohol | Ethanol to 100% |
| 7(G) | 5 | 0.5 | 0.5 | 0.75 | q.s. |
| 7(H) | 10 | 0.5 | 0.5 | 0.75 | q.s. |
| 7(I) | Comparative PENLAC ™ Nail Lacquer Solution Topical Solution 8% | | | | |

Note:
Ex. 7(I) contains 80 mg ciclopirox in a solution base consisting of ethyl acetate, NF; and butyl monoester of poly[methylvinylether/maleic acid] in isopropyl alcohol (Dermik Laboratories, Inc.).

EXAMPLE 8

This example illustrates the fungicidal activity of one-coat type dual action, antifungal nail coat compositions containing terbinafine hydrochloride and, as a penetration enhancer, DDAIP.HCl, against three strains of the dermatophyte *Trichopyton rubrum* (*T. rubrum*), nine strains of the dermatophyte *Trichophyton mentagrophytes* (*T. mentagrophytes*), and ten strains of the yeast *Candida albicans* (*C. albicans*).

Nail coat compositions containing terbinafine hydrochloride, Exs. 8(A), 8(B), and drug free control, Ex. 8(C) were prepared having the amounts shown in Table 6 and fungicidal efficacy compared against that of a commercial composition, Ex. 8(D): PENLAC™ Nail Lacquer Solution Topical Solution 8% (Containing ciclopirox).

TABLE 6

| | Weight Percent Ingredient | | | | |
|---|---|---|---|---|---|
| Example | Terbinafine HCl | DDAIP•HCl | PVP, USP | Benzyl Alcohol | Ethanol to 100% |
| 8(A) | 1 | None | 0.5 | 0.75 | q.s. |
| 8(B) | 1 | 0.5 | 0.5 | 0.75 | q.s. |
| 8(C) | None | 0.5 | 0.5 | 0.75 | q.s. |
| 8(D) | Comparative PENLAC ™ Nail Lacquer Solution Topical Solution 8% | | | | |

Note:
Ex. 8(D) contains 80 mg ciclopirox in a solution base consisting of ethyl acetate, NF; and butyl monoester of poly[methylvinylether/maleic acid] in isopropyl alcohol (Dermik Laboratories, Inc.).

Fungicidal efficacy, based on minimum inhibitory concentration (MIC) and minimum fungicidal concentration (MFC) of the drug, was evaluated using a broth microdilution assay, as well as an agar diffusion plate assay, measuring the zones of inhibition.

The broth microdilution method was a modification of a NCCLS M38-A standard method for the susceptibility testing of conidium-forming filamentous fungi of the National Committee for Clinical Laboratory Standards (NCCLS). The modified method was developed at the Center for Medical Mycology, University Hospitals of Cleveland, Cleveland, Ohio, based on the method described in Jessup, et al., "Antifungal Susceptibility Testing of Dermatophytes: Establishing a Medium for Inducing Conidial Growth and Evaluation of Susceptibility of Clinical Isolates," *Journal of Clinical Microbiology*, 38, 341-344, published by the American Society for Microbiology (2000), the disclosures of which are incorporated herein by reference. Based on a multicenter study of the reproducibility of the modified method for testing dermatophytes, adoption of the modified method as an amendment to the NCCLS M38-A standard has been proposed. The modified method is described below.

Dermatophyte isolates are subcultured onto Potato Dextrose Agar (PDA) and incubated at a temperature of about 30° C. for a period of about 4 to about 5 days or until good conidiation is produced. T rubrum isolates are subcultured onto cereal (oatmeal) agar instead of PDA in order to induce conidia production. A suspension of conidia in sterile saline is made by gently swabbing the colony surface with a sterile swab. The suspension is allowed to settle for about 5 to about 10 minutes and the conidia is counted using a hemocytometer. Working suspensions of conidia are prepared in 10 ml RPMI 1604 (Difco Laboratories) medium to a final concentration of 1 to $3 \times 10^3$ CFU/ml. Yeast controls are subcultured onto PDA and incubated at a temperature of about 35° C. for about 48 hours. Yeast inocula are prepared to a final concentration of 0.5 to $2.5 \times 10^3$ CFU/ml. For MIC assay, each drug concentration well and growth control well is inoculated with 100 microliters of cell suspension, and the final volume in each microtiter well is 200 microliters. The dermatophyte plates are incubated at a temperature of about 35° C. for 4 days (yeast controls for 48 hours). Plates are examined visually for 50% and 80% growth inhibition as compared to the growth control, and MIC results are recorded in micrograms (μg)/ml. The MIC endpoint is generally defined as the lowest concentration that inhibited 80% of fungal growth as compared to the growth control. To perform the MFC assay, 100 μl is removed from each microtiter well without visible growth and subcultured onto Potato Dextrose Agar plates. The lowest concentration to produce <1-2 colonies is considered the MFC. (Inoculum removed from the microtiter wells is streaked for isolation—there are no zones of inhibition).

For the MIC assay, a broth dilution is performed in microtiter wells with RPMI 1064 as the diluent. The MFC assay is performed by subculturing the microtiter wells from the MIC test.

For the agar diffusion assay, the standardized inoculum of conidia is applied to the surface of a Potato Dextrose Agar plate and allowed to dry. Wells are then cut into the agar and the test composition is put into the wells and allowed to diffuse and antifungal activity is evidenced by zones of growth inhibition (i.e., area remaining clear, lacking growth) on the surface of the plates measured in millimeters (mm) diameter.

An agar diffusion assay was performed using Potato Dextrose Agar plates seeded with a lawn of conidial suspension at a concentration of $5 \times 10^5$ CFU/ml. The plates were inoculated separately with undiluted test compositions of Exs. 8(A-D) by adding 200 μl of undiluted test compositions to wells cut into the agar and allowed to diffuse. The inoculated plates were then incubated at about 35° C. for 4 days for dermatophytes and 48 hours for yeast. The range and mean diameter in millimeters (mm) measurement of the Zone of Inhibition (Zone) assays of the nail compositions in Table 6 are summarized in Table 6-A below.

TABLE 6-A

| Organism | Ex. 8(A) Zone (mm) | | Ex. 8(B) Zone (mm) | | Ex. 8(C) Zone (mm) | | Ex. 8(D) Zone (mm) | |
|---|---|---|---|---|---|---|---|---|
| | Range | Mean | Range | Mean | Range | Mean | Range | Mean |
| *T. mentagrophytes*, n = 9 | 95-100 | 97.9 | 95-100 | 97.4 | 13-18 | 16 | 30-36 | 32.2 |
| *T. rubrum*, n = 3 | 55-100 | 84.3 | 50-98 | 81 | 16-18 | 17.3 | 30-34 | 32 |
| *C. albicans*, n = 10 | 19-30 | 23.7 | 18-30 | 23.8 | 0-10 | 8.5 | 18-30 | 25.1 |

The data in Table 6-A show that terbinafine-containing nail coat compositions, Exs. 8(A) and 8(B) were fungicidally active against all three organisms and substantially equivalent in activity to one another. The drug-free composition, Ex. 8(C) was judged substantially ineffective against the yeast, and weakly effective against the two dermatophytic fungi, indicating that such activity was likely attributable to antimicrobial effects contributed by benzyl alcohol and ethanol. The terbinafine-containing nail coat compositions were judged about three times more effective against the dermatophytic fungi, *T. mentagrophytes*, and *T. rubrum*, than the commercial ciclopirox-containing nail lacquer, and were substantially equivalent to the commercial nail lacquer against the yeast, *C. albicans*.

EXAMPLE 9

The fungicidal activity of terbinafine hydrochloride against the dermatophytic fungi, *T. mentagrophytes*, (ATCC 24953), is illustrated in the modified NCCLS broth dilution assay described in Example 8, based on minimum inhibitory concentration (MIC) and minimum fungicidal concentration (MFC) as well as an agar diffusion plate assay measuring the zones of inhibition.

A placebo composition, Ex. 9(A), two nail coat compositions containing terbinafine hydrochloride, Exs. 9(B) and 9(C), and a drug-free comparative composition, Ex. 9(D) were prepared having the amounts shown in Table 7. Also prepared were dimethylsulfoxide (DMSO) solvent solutions of terbinafine hydrochloride, of the penetration enhancer, DDAIP.HCl, and combinations thereof (Exs. 9(E-H) in the amounts also shown in Table 7. Included for comparison, was the commercial PENLAC™ Nail Lacquer solution.

TABLE 7

| | Weight Percent Ingredient | | | | |
|---|---|---|---|---|---|
| Example | Terbinafine HCl | DDAIP•HCl | PVP, USP | Benzyl Alcohol | Ethanol to 100% |
| 9(A) (control) | None | None | 0.5 | 0.75 | q.s. |
| 9(B) | 1 | 0.5 | 0.5 | 0.75 | q.s. |
| 9(C) | 1 | None | 0.5 | 0.75 | q.s. |
| 9(D) | None | 0.5 | 0.5 | 0.75 | q.s. |
| 9(E) | None | 1 mg/ml in DMSO | None | None | None |
| 9(F) | 1 mg/ml in DMSO | None | None | None | None |
| 9(G) | 1 µg/ml in DMSO | None | None | None | None |
| 9(H) | 1 µg/ml in DMSO | 1 µg/ml in DMSO | None | None | None |
| 9(I) | Comparative PENLAC ™ Nail Lacquer Solution Topical Solution 8% | | | | |

Note:
Ex. 9(I) contains 80 mg ciclopirox in a solution base consisting of ethyl acetate, NF; isopropyl alcohol, USP; and butyl monoester of poly[methylvinylether/maleic acid] in isopropyl alcohol (Dermik Laboratories, Inc.).

MIC assay was determined using the broth dilution procedure described in Example 8 performed in microtiter wells with RPMI 1604 as the diluent. Serial dilutions of each test composition were made in RPMI diluent, and then 100 µl of undiluted test composition and of each diluted composition was added to a respective microtiter well. Conidial suspension (100 µl) was then added to each well and the plates were incubated at an incubation temperature of about 35° C. for an incubation period of 4 days dermatophytes, and 48 hours for yeasts. For MFC determination, undiluted test composition was added to wells cut into the agar and allowed to diffuse. The MIC endpoint was the lowest concentration that inhibited 80% of fungal growth as compared to the growth control. The MFC endpoint was the lowest concentration to produce 1-2 colonies. The zone of inhibition size was measured (diameter of area remaining clear, i.e., lacking growth).

The zone of inhibition (diameter size in mm), and the dilution factors for the MIC and MFC assays obtained with each of the compositions is shown in Table 7-A.

TABLE 7-A

| Example No. | Zone size (mm) | Dilution (Composition:Diluent) | |
|---|---|---|---|
| | | MIC | MFC |
| 9(A) | Zero | 1:32 | 1:16 |
| 9(B) | 80 | >1:512 | >1:512 |
| 9(C) | 82 | >1:512 | >1:512 |
| 9(D) | Zero | 1:64 | 1:32 |
| 9(E) | Zero | 1:32 | 1:4 |
| 9(F) | 80 | >1:512 | >1:512 |
| 9(G) | 18 | 0.03 µg/ml | 0.125 µg/ml |
| 9(H) | 18 | 0.03 µg/ml | 0.125 µg/ml |
| 9(I) | 33 | >1:512 | >1:512 |

The terbinafine-containing nail coat compositions, Exs. 9(B) and 9(C) were fungicidal at the highest dilution (>1:512). The terbinafine-free compositions, Exs 9(A) and 9(D) were weakly fungicidal, based on MIC assays, but produced no zone of inhibition, indicating that any inhibitory effect observed was likely attributable primarily to some antimicrobial contribution from the benzyl alcohol and ethanol in the vehicle. The terbinafine-containing compositions were judged about 2.4 times as effective as the commercial nail lacquer, Ex. 9(I), at equivalent volume concentrations, based on the zone of inhibition. The commercial nail lacquer was comparable to the terbinafine-containing compositions, based on MIC and MFC assays. Some difficulty was encountered with the commercial nail lacquer at the highest concentrations due to evaporation of the lacquer vehicle and hardening of the lacquer in the microtiter well.

In DMSO solvent, the fungicidal efficacy at a dilution of >1:512 of terbinafine hydrochloride at 1 mg/ml concentration was again confirmed by Ex. 9(F), with at most some weak efficacy from the penetration enhancer alone (Ex. 9(E)) based on MIC. At a terbinafine hydrochloride concentration of 1 μg/ml, the fungicidal efficacy of the terbinafine hydrochloride was substantially equivalent with or without the penetration enhancer present (Exs. 9(G), 9(H)).

The foregoing is intended to be illustrative of the present invention, but not limiting. Numerous variations and modifications may be effected without departing from the true spirit and scope of the invention.

The invention claimed is:

1. An antifungal nail coat composition consisting of, on a total composition weight basis:
   10 weight percent terbinafine hydrochloride;
   0.5 weight percent dodecyl-2-(N,N-dimethylamino) isopropionate hydrochloride;
   0.75 weight percent benzyl alcohol;
   0.5 weight percent polyvinylpyrrolidone; and
   the remainder ethanol.

* * * * *